(12) United States Patent
Williams

(10) Patent No.: US 7,285,427 B2
(45) Date of Patent: Oct. 23, 2007

(54) RAMAN-ACTIVE PARTICLES AND METHODS OF MAKING AND USING THEM

(75) Inventor: Darryl Stephen Williams, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 266 days.

(21) Appl. No.: 10/960,173

(22) Filed: Oct. 6, 2004

(65) Prior Publication Data

US 2006/0073612 A1   Apr. 6, 2006

(51) Int. Cl.
G01N 33/553   (2006.01)

(52) U.S. Cl. .................................... 436/525

(58) Field of Classification Search ............... 436/525, 436/514, 518, 523, 524, 526; 435/4, 7.1, 435/7.92, 287.1–287.3, 288.7; 422/55
See application file for complete search history.

(56) References Cited

U.S. PATENT DOCUMENTS

| | | | |
|---|---|---|---|
| 4,071,298 A | | 1/1978 | Falconer |
| 4,127,329 A | | 11/1978 | Chang et al. |
| 4,638,032 A | * | 1/1987 | Benner .................. 525/54.11 |
| 5,376,556 A | * | 12/1994 | Tarcha et al. ............. 436/525 |
| 6,025,202 A | | 2/2000 | Natan |
| 6,052,183 A | | 4/2000 | Lee |
| 6,124,142 A | | 9/2000 | Fujino et al. |
| 6,149,868 A | | 11/2000 | Natan et al. |
| 6,180,415 B1 | * | 1/2001 | Schultz et al. ............. 436/518 |
| 6,219,137 B1 | | 4/2001 | Vo-Dinh |
| 6,242,264 B1 | | 6/2001 | Natan et al. |
| 6,514,767 B1 | | 2/2003 | Natan |
| 6,624,886 B2 | | 9/2003 | Natan et al. |
| 6,675,106 B1 | | 1/2004 | Keenan et al. |
| 2004/0086897 A1 | | 5/2004 | Mirkin et al. |
| 2005/0147976 A1 | * | 7/2005 | Su ................................ 435/6 |
| 2006/0038979 A1 | * | 2/2006 | Natan et al. ................... 356/71 |

FOREIGN PATENT DOCUMENTS

WO   WO02/040698 A2   11/2001
WO   WO2004/007767 A2   7/2003

OTHER PUBLICATIONS

"Glass-Coated, Analyte-Tagged Nanoparticles: A New Tagging System Based on Detection with Surface-Enhanced Raman Scattering", S.P. Mulvaney, M.D. Musick, C.D. Keating, and M.J. Natan, Langmuir 2003, 19, pp. 4784-4790.
"Raman Spectroscopy", S.P. Mulvaney and C.D. Keating, Analytical Chemistry, vol. 72, No. 12, Jun. 15, 2000, pp. 145R-157R.
International Search Report, Dec. 4, 2006.

* cited by examiner

*Primary Examiner*—Ann Yen Lam
(74) *Attorney, Agent, or Firm*—William E. Powell, III; Curtis B. Brueske

(57) ABSTRACT

A Raman-active particle as well as a method of making a Raman-active particle are described. The Raman-active particle includes a core particle and a coating. The coating substantially covers the core particle. A Raman-active analyte is at least partially within the coating. The method of making a Raman-active particle includes i) providing a colloidal solution comprising a core particle; ii) providing a coating or coating precursor to the colloidal solution to form a resulting solution; and iii) providing a Raman-active analyte to the resulting solution. A method of conducting an assay is also described. The method includes: i) attaching a Raman-active particle to a targeted moiety; ii) measuring the Raman spectrum of the Raman-active particle; and iii) correlating the Raman spectrum to the presence of the targeted moiety.

23 Claims, 17 Drawing Sheets

RAMAN-ACTIVE PARTICLES AND METHODS OF MAKING AND USING THEM

BACKGROUND OF THE INVENTION

The present invention generally relates to Raman-active particles and methods of making and using the same, and more particularly relates to Raman-active particles with an analyte at least partially within a coating of the Raman-active particle and methods of making the same.

DESCRIPTION OF RELATED ART

In some known technologies, a Raman-active analyte is incorporated into a material, such as the Raman-active particle referred to in U.S. Pat. No. 6,514,767. Some Raman-active particles, as in U.S. Pat. No. 6,514,767, typically have a core particle (also referred to as a core), a Raman-active analyte, and a coating, (also referred to as an encapsulant). Typically, a linker is provided which allows the deposition of a coating material onto the core particle. The coating inhibits Raman-active particles from aggregating. A conventional Raman-active particle 10 is illustrated in FIG. 1 as including a coating 14 surrounding a core particle 12 and an analyte 16.

Known methods of making Raman-active particles 10 involve incorporating a Raman-active analyte into the Raman-active particles 10 before a coating solution is added. A disadvantage with adding the analyte 16 before initiating the coating 14 is uncontrolled aggregation of core particles 12. Aggregation occurs because the analyte 16, which causes core aggregation and flocculation, binds more strongly to the surface of the core particle 12 than the linker, thereby displacing the linker. The analyte 16 binds more strongly to the core particle than the linker even before the coating 14 begins to form and colloid flocculation can occur. In some known methods, the amount of analyte 16 added is equal to the amount of linker added, enhancing the likelihood that colloid flocculation will occur, since the analyte 16 could theoretically completely displace the linker.

Thus, an improved method of making Raman-active particles that addresses some of the deficiencies exhibited by known methods is still needed. Also needed are Raman-active particles that address some of the deficiencies exhibited in known Raman-active particles.

SUMMARY

The purpose and advantages of embodiments of the invention will be set forth and apparent from the description of exemplary embodiments that follows, as well as will be learned by practice of the embodiments of the invention. Additional advantages will be realized and attained by the methods and systems particularly pointed out in the written description and claims hereof, as well as from the appended drawings.

An embodiment of the invention provides a Raman-active particle. The Raman-active particle includes a core particle and a coating. The coating substantially covers the core particle and a Raman-active analyte is at least partially within the coating.

A second embodiment provides a method of making a Raman-active particle. The method includes: i) providing a colloidal solution comprising a core particle and ii) providing a coating or coating precursor to the colloidal solution to form a resulting solution; and iii) providing a Raman-active analyte to the resulting solution.

A third embodiment provides a method of conducting an assay. The method includes: i) attaching a Raman-active particle to a targeted moiety; ii) measuring a Raman spectrum of the Raman-active particle; and iii) correlating the Raman spectrum to the presence of the targeted moiety. The Raman-active particle includes: a core particle and a coating. The coating substantially covers the core particle and a Raman-active analyte is at least partially within the coating.

A fourth embodiment provides a Raman-active particle. The Raman-active particle includes a core particle with a metallic surface and a coating. The coating substantially covers the core particle and includes silica. A Raman-active analyte is at least partially within the coating.

A fifth embodiment provides a method of making a Raman-active particle. The method includes: i) providing a colloidal solution comprising a core particle; ii) providing a coating or coating precursor to the colloidal solution to form a resulting solution; and iii) providing a Raman-active analyte to the resulting solution. The core particle has a metallic surface and the coating includes silica.

The accompanying figures, which are incorporated in and constitute part of this specification, are included to illustrate and provide a further understanding of the method and system of the invention. Together with the description, the drawings serve to explain the principles of the invention.

DETAILED DESCRIPTION OF EXEMPLARY EMBODIMENTS

Reference will now be made in detail to exemplary embodiments of the invention which are illustrated in the accompanying figures and examples.

Figure 1:
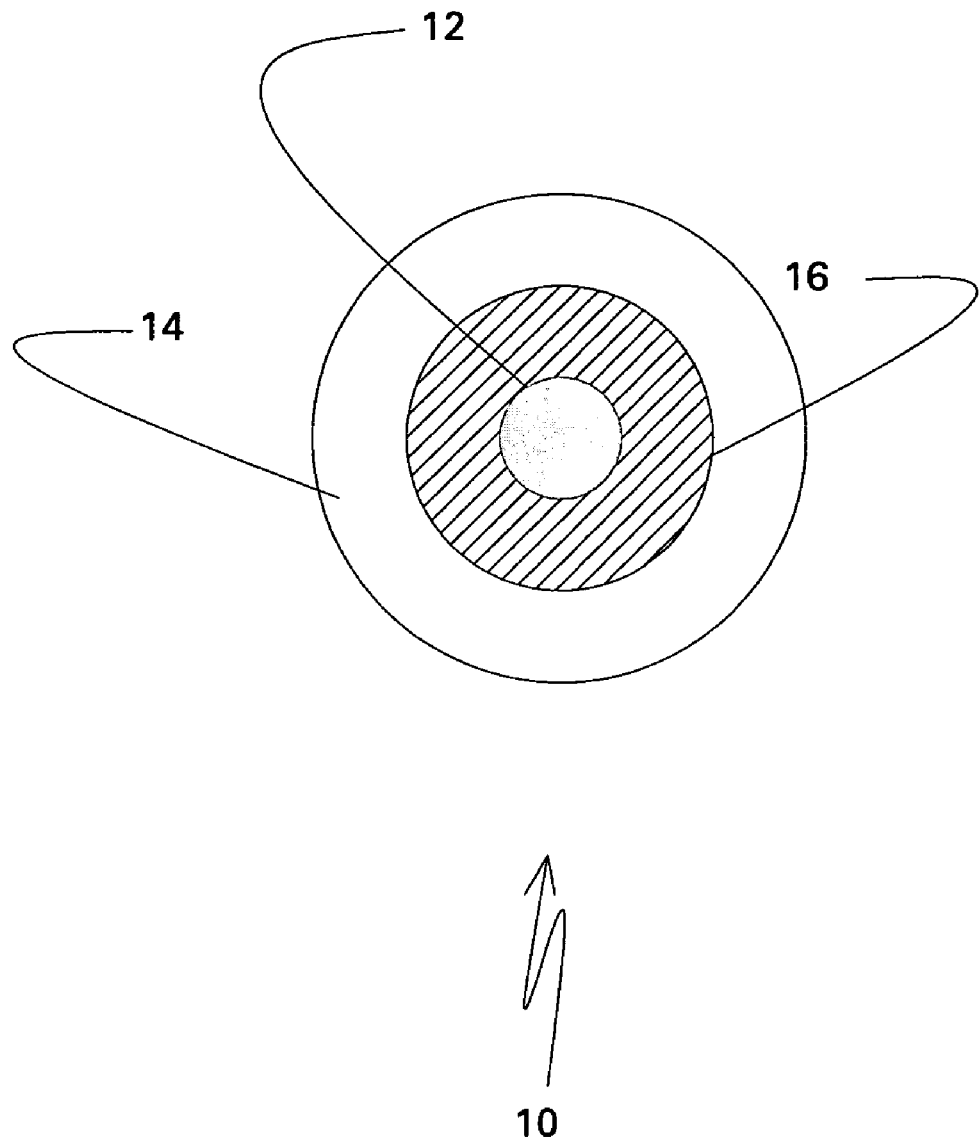
FIG. 1 is a schematic representation of a known Raman-active particle.
Figure 2:
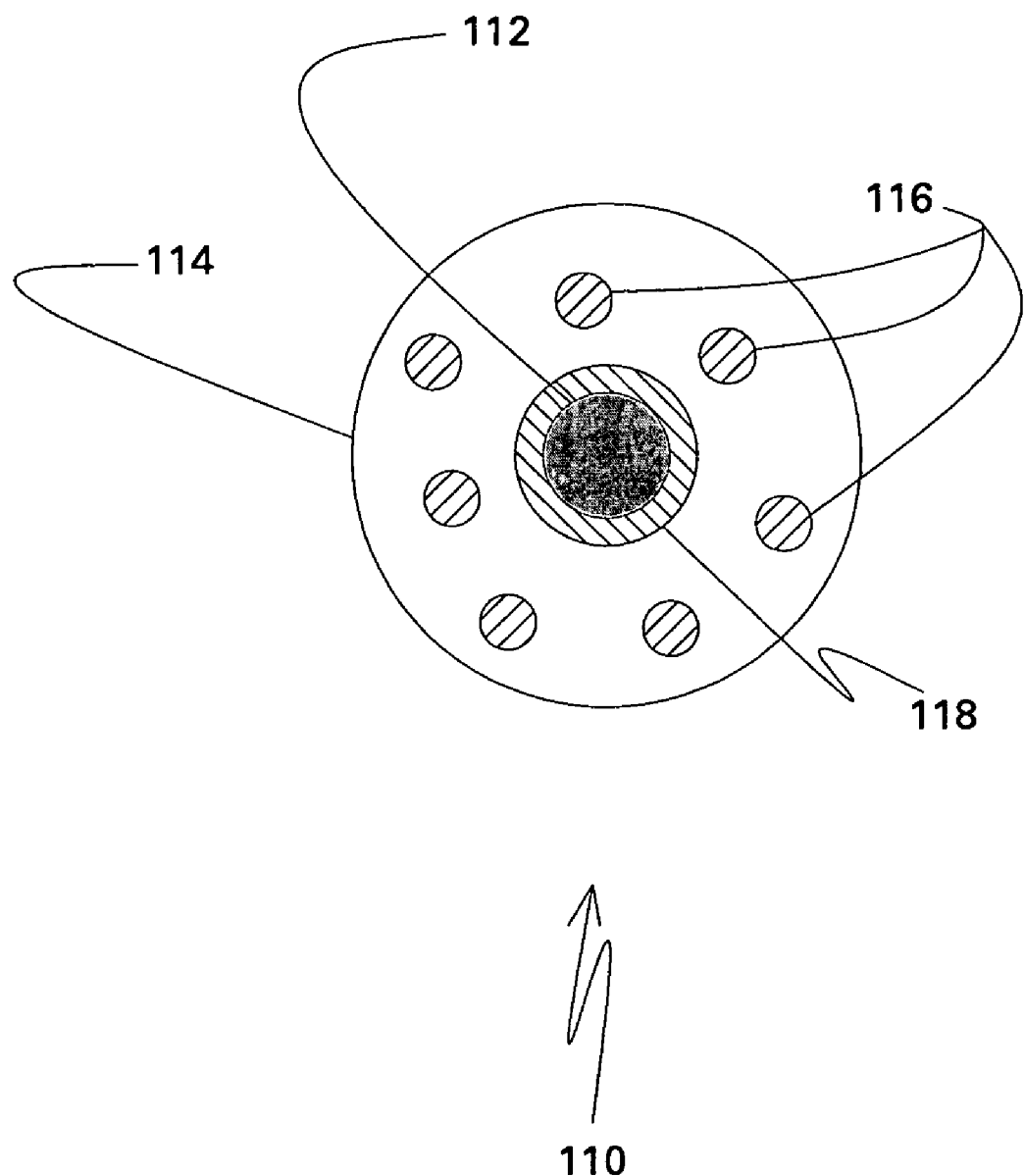
FIG. 2 is a schematic representation of a Raman-active particle wherein the analyte is dispersed within the coating in accordance with an embodiment of the invention.

With reference to FIG. 2, there is shown one embodiment of a Raman-active particle 110 that includes a core particle 112, a coating 114, and a Raman-active analyte 116. It should be appreciated that one or more core particles 112, coatings 114, and analytes 116 may be included within the Raman-active particle 110. The analyte 116 is at least partially within the coating 114 and the coating 114 substantially covers the core particle 112.

In one embodiment, the core particle 112 has a metallic surface. The core particle 112 may include a metal selected from a group consisting of Au, Ag, Cu, Ni, Pd, Pt, Na, Al, and Cr, either individually or through any combination thereof. The core particle 112 may include any other inorganic or organic material provided the surface of the particle is metallic. In a particular embodiment, the core particle 112 comprises Au.

The shape of the core particle 112 may vary. For example, the core particle 112 may be in the shape of a sphere, fiber, plate, cube, tripod, pyramid, rod, tetrapod, or any non-spherical object. In one embodiment, the core particle 112 is substantially spherical.

The size of the core particle 112 also may vary and can depend on its composition and intended use. In one embodiment, the core particles 112 have an average diameter in a range from about 1 nm to about 500 nm. In another embodiment, the core particles 112 have an average diameter in a range from about 12 nm to about 100 nm.

The coating 114 includes a material whose function is to stabilize a Raman-active particle 110 against aggregation. The coating 114 stabilizes the Raman-active particle 110 in one way by inhibiting aggregation of Raman-active particle 10. The coating 114 is sufficiently thick to stabilize the Raman-active particle 110. In one embodiment, the coating 114 has a thickness in a range from about 1 nm to about 500 nm. In another embodiment, the coating 114 has a thickness in a range from about 5 nm to about 30 nm.

In one embodiment, the coating 114 comprises an elemental oxide. In a particular embodiment, the element in the elemental oxide includes silicon. The percentage of silicon may be varied and is dependent on several factors. Such factors may include the intended use of the Raman-active particle 110, the composition of the core particle 112, the degree to which the coating 114 is to be functionalized, the desired density of the coating 114 for a given application, the desired melting point for the coating 114, the identity of any other materials which constitute the coating 114, and the technique by which the Raman-active particle 110 is to be prepared. In one embodiment, the element in the elemental oxide of the coating 114 includes at least about 50-mole % silicon. In another embodiment, the element in the elemental oxide of the coating 114 includes at least about 30-mole % silicon. [Yet, in another embodiment, the element in the elemental oxide of the coating 114 comprises substantially silicon.]

In yet another embodiment, the coating 114 includes a composite coating. A composite coating comprises oxides of one or more elements selected from a group consisting of Si, B, Al, Ga, In, Sc, Y, La, Ti, Zr, Hf, V, Nb, Ta, Cr, Mn, Fe, Co, Ni, Li, Na, K, Rb, Cs, Be, Mg, Ca, Sr, Ba, Zn, Cd, Ge, Sn, and Pb. Furthermore, the coating 114 may include multilayer coatings 114. Each of the coating layers 114 in the multilayer coating 114 individually may include different coating compositions, such as 50-mole % silicon oxide in one coating layer and a composite coating in another coating layer.

The Raman-active particle 110 includes one or more Raman-active analytes 116. The Raman-active analyte 116 is a molecule which exhibits Raman scattering when in the vicinity of a metallic surface of a core particle 112. Examples of Raman-active analytes 116 include, but are not limited to, 4-mercaptopyridine, 2-mercaptopyridine (MP), trans-bis(pyridyl)ethylene (BPE), naphthalene thiol (NT), and mercaptobenzoic. The Raman-active analyte 116 may either individually include 4-mercaptopyridine, 2-mercaptopyridine, trans-bis(pyridyl)ethylene, naphthalene thiol, mercaptobenzoic acid or any combination thereof.

Figure 3:
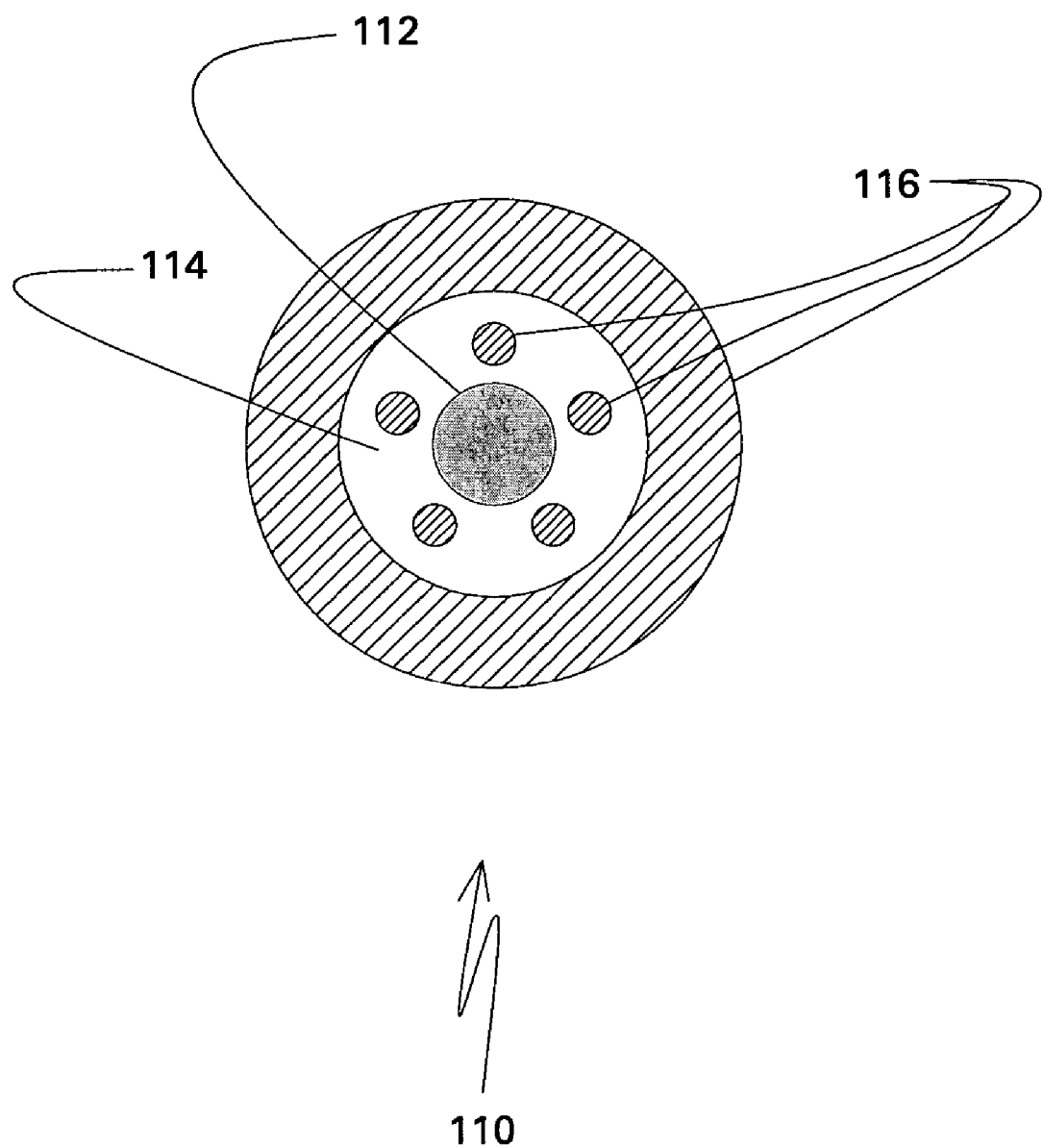
FIG. 3 is a schematic representation of a Raman-active particle wherein the analyte partially surrounds a coated Raman-active particle in accordance with an embodiment of the invention.
Figure 4:
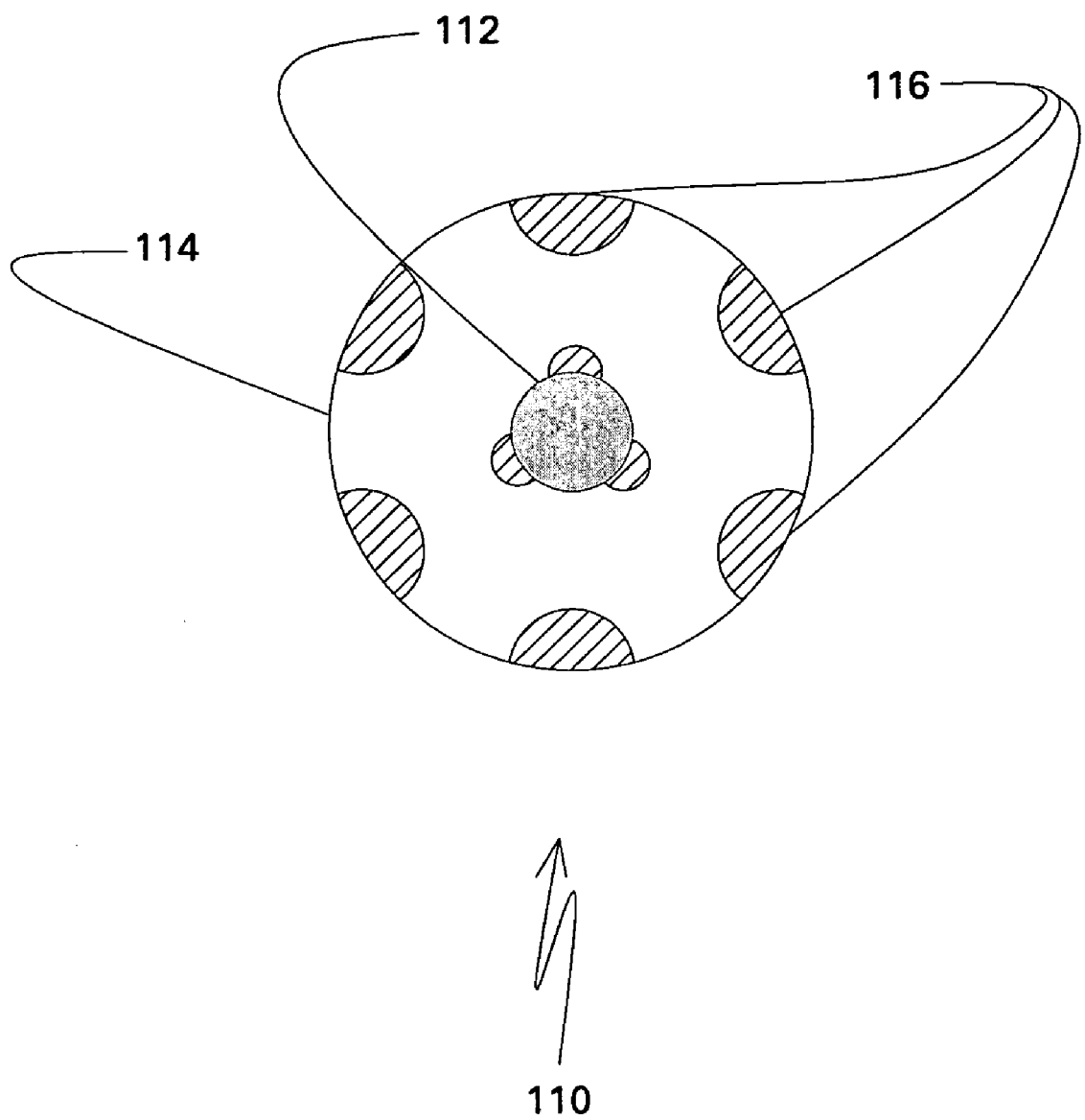
FIG. 4 is a schematic representation of a Raman-active particle wherein the analyte is embedded within the coating in accordance with an embodiment of the invention.

The Raman-active analyte 116 is at least partially within the coating 114. FIGS. 2-4 are schematic representations of the Raman-active analyte 116 at least partially within the coating 114. The Raman-active analyte 116 can be at least partially within the coating 114 in various orientations, such as, but not limited to, dispersed within the coating 114 as in FIG. 2, within and around the coating 114 as in FIG. 3, or embedded within the coating 114 as in FIG. 4. Furthermore, a plurality of analytes 116 may be within the coating 114. The plurality of analytes 116 may be within the coating 114 at a plurality of sites or at a single site. It should be appreciated that each of the analytes 116 may be within the coating 114 by a different mode, such as dispersed within the coating 114 as in FIG. 2, around the coating as in FIG. 3, or embedded within the coating 114 as in FIG. 4.

Figure 5:
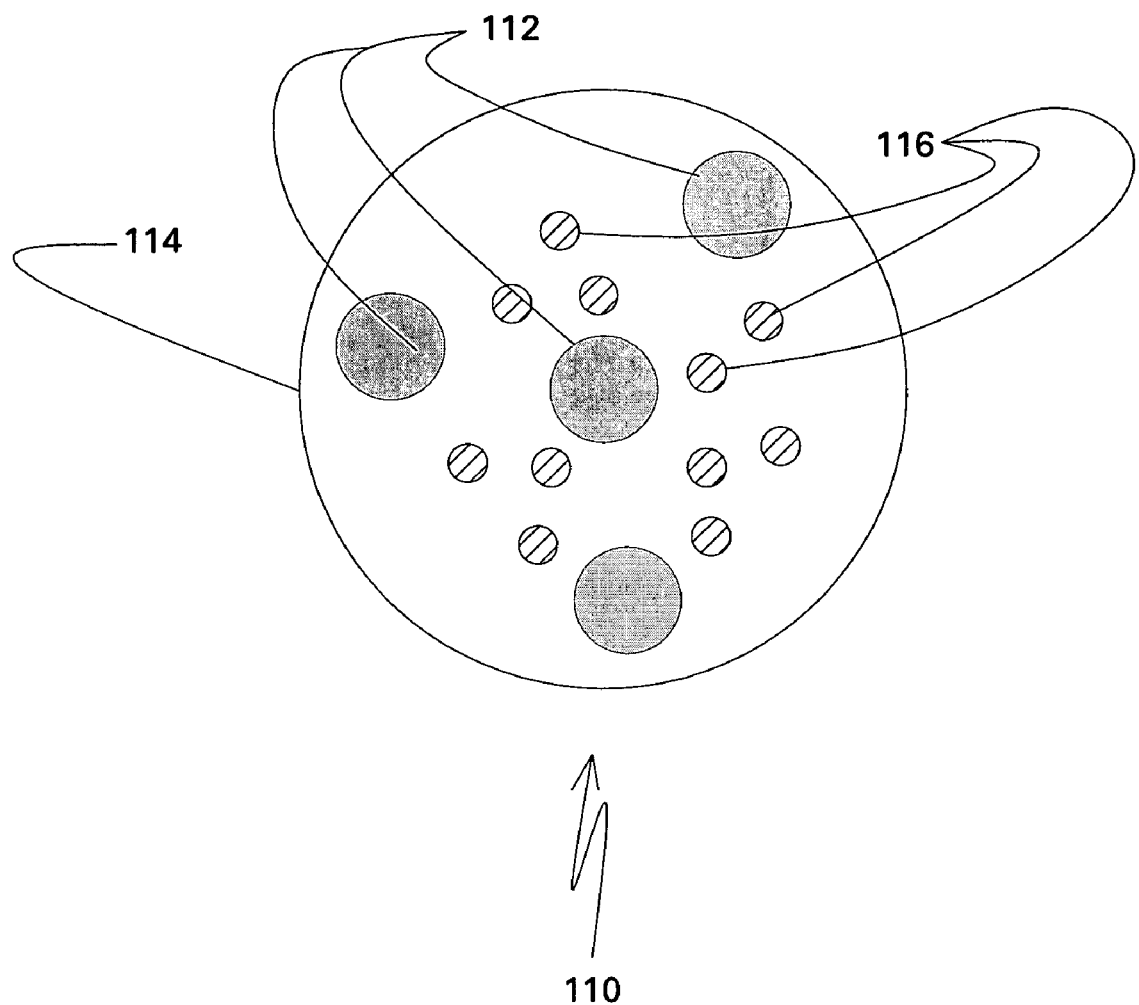
FIG. 5 is a schematic representation of a Raman-active particle with a plurality of core particles in accordance with an embodiment of the invention.
Figure 6:
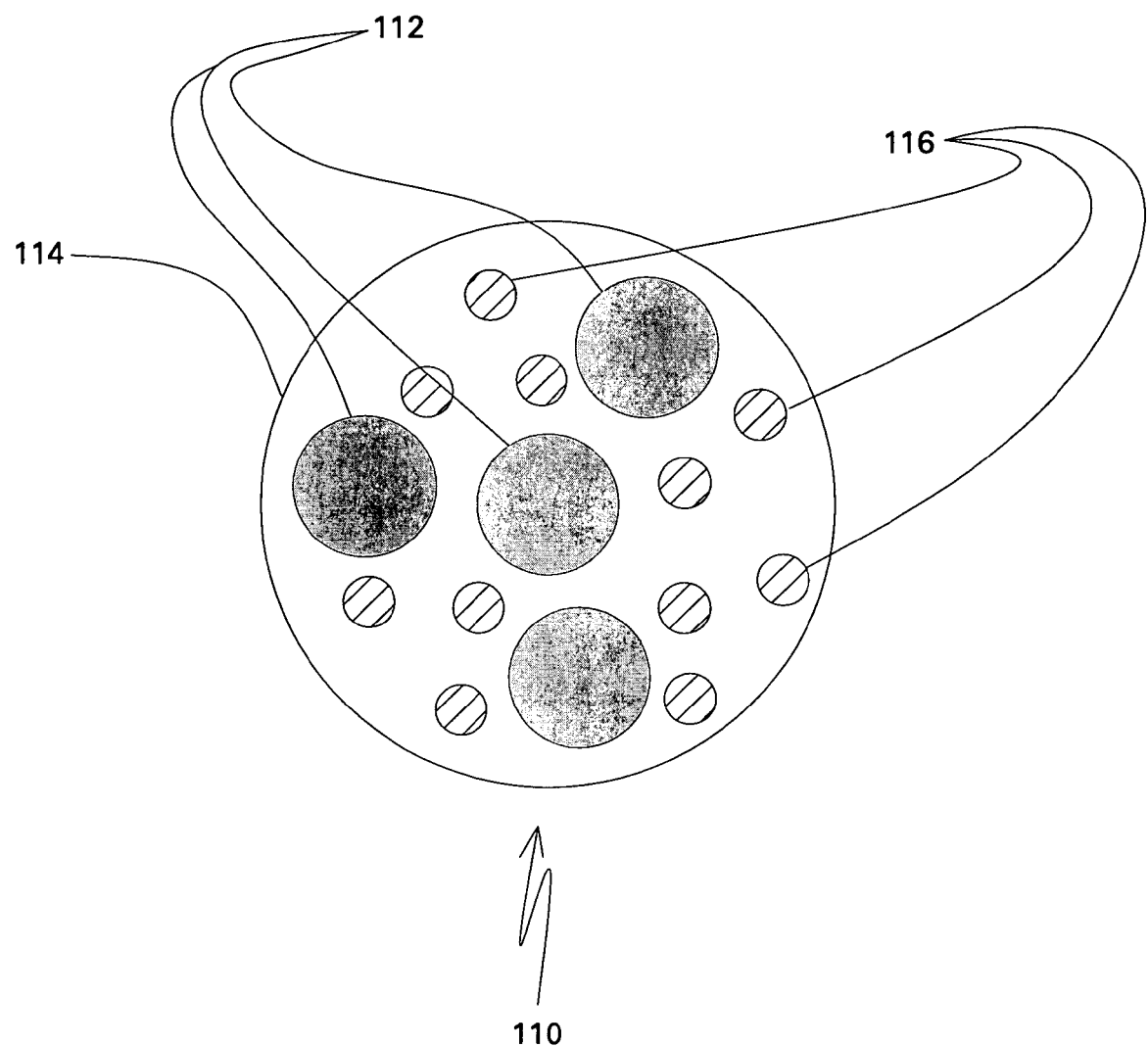
FIG. 6 is a schematic representation of a Raman-active particle with a plurality of core particles in accordance with an embodiment of the invention.

The Raman-active particle 110 may include one core particle 112 within a coating 114 as in FIGS. 2-4 or multiple core particles 112 within a coating 114 as in FIGS. 5-6. The multiple core particles 112 are non-aggregated as in FIG. 5 or closer together as in FIG. 6. There may be particular advantages associated with Raman-active particles 110 that have one core particle 112 within a coating 114 or multiple core particles 112 within a coating 114. The selection as to how many core particles 112 should be contained within a coating 114 may depend largely on the particular application for which the Raman-active particles 110 are being used. Adjusting process conditions may be effective in obtaining Raman-active particles 110 with a single core particle 112 contained in the coating 114. For example, the coating 114 may also stabilize a core particle 112 against aggregating with another core particle 112.

The Raman-active particle 110 may vary in shape and size. In one embodiment, the Raman-active particles 110 are substantially spherical and have an average diameter in a range of up to about 1000 nm.

In one embodiment, the Raman-active particle 110 includes one or more linkers 118, as in FIG. 2. The linker 118 binds to the core particle 112 and provides an interaction with the coating 114. The linker 118 allows or facilitates the coating 114 to attach to the core particle 112. The linker 118 may be a molecule comprising a functional group, which can bind to the metal surface of the core particle 112, and a functional group onto which the coating 114 can deposit, such as alkoxysilanes. Examples of alkoxysilanes include trialkoxysilanes. Trialkoxysilane linkers 118 which may be used to deposit coatings 114 comprising silica include, but are not limited to, aminopropyl trimethoxysilane (APTMS), aminopropyl triethoxysilane, mercaptopropyl trimethoxysilane, mercaptopropyl triethoxysilane, hydroxypropyl trimethoxysilane, and hydroxypropyl triethoxysilane, either individually or through any combinations thereof.

When more than one analyte 116, coating 114, linker 118, and core particle 112 are present, its definition on each occurrence is independent of its definition at every other occurrence. Also, combinations of an analyte 116, coating 114, linker 118, and core particle are permissible only if such combinations result in stable Raman-active particles 110. Also, methods in the combinations of an analyte 116, coating 114, linker 118, and core particle are permissible only if such combinations result in stable Raman-active particles 110.

Figure 7:
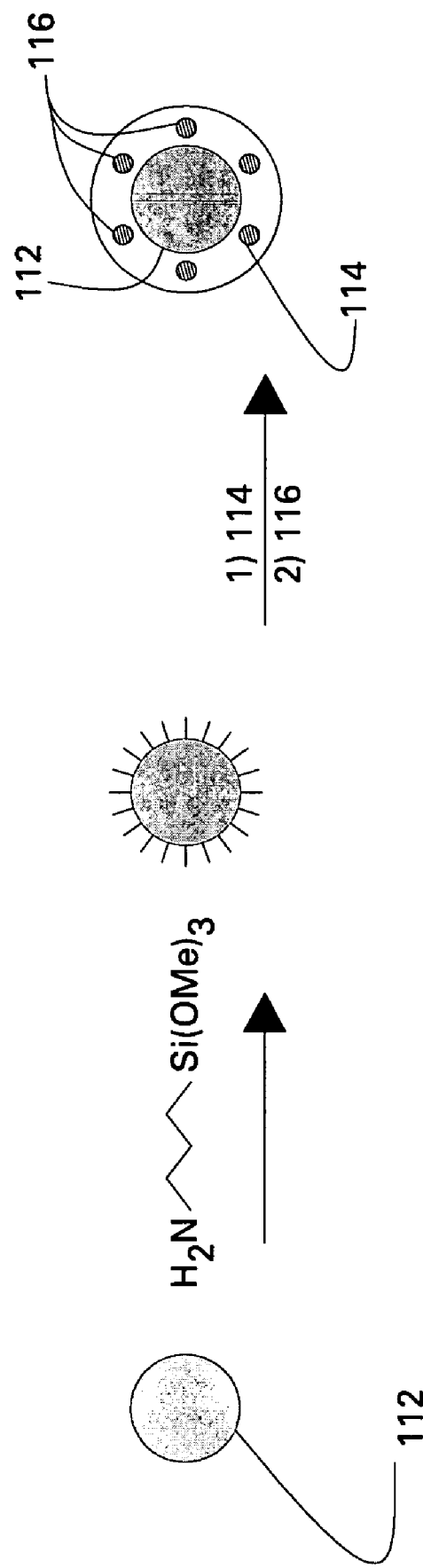
FIG. 7 is a schematic representation of a method of making a Raman-active particle in accordance with an embodiment of the invention.
Figure 8:
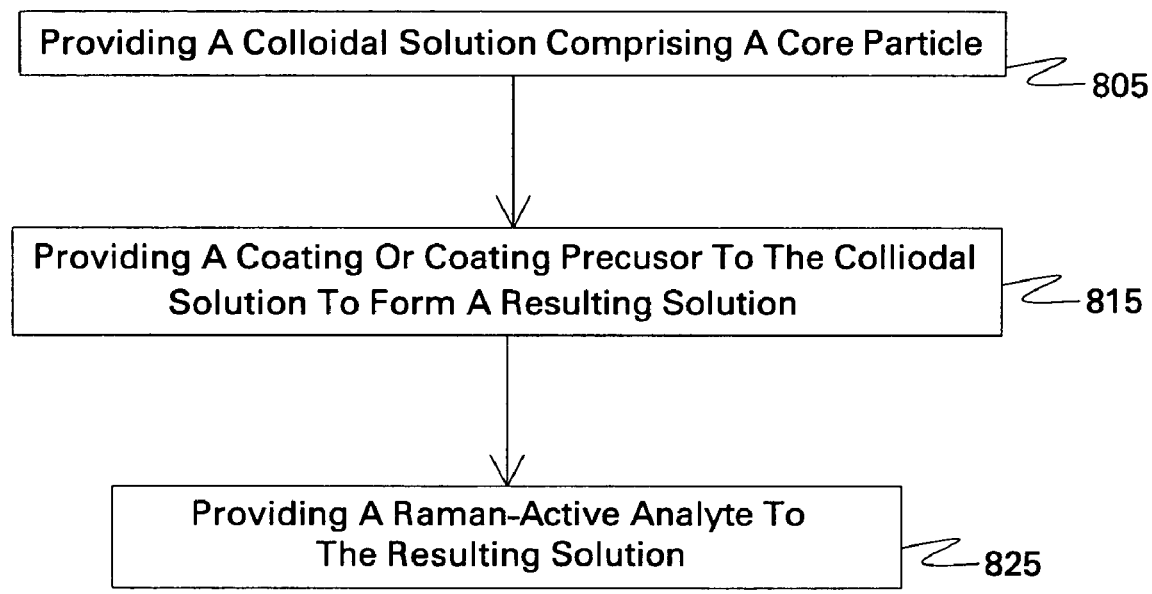
FIG. 8 is a flow chart of a method of making a Raman-active particle in accordance with an embodiment of the invention.

With reference to FIGS. 7 and 8, next will be described a method of making a Raman-active particle 110. FIG. 7 is a schematic representation of a method of making the Raman-active particle 110. FIG. 8 is a flow chart of method steps for making the Raman-active particle 110.

The method includes, at step 805, providing a colloidal solution comprising a core particle 112. The core particle 112 may be an Au particle. The average size of the Au particles and amount of the colloidal solution may vary, such as for example, 50 mL of a 50 nm Au particles. The Au particle may be treated with ion exchange resin and filtered prior to beginning the coating reaction.

At step 815, a coating 114 and or a coating precursor is provided to the colloidal solution comprising a core particle 112 to form a resulting solution. The resulting solution may either individually comprise a coating, a coating precursor, or a combination thereof. The coating 114 or coating precursor at least partially coats the core particle 112. The coating precursor may be provided in the form of a sodium silicate solution or any other source of silica.

At step 825, at least one Raman-active analyte 116 is provided to the resulting solution. The at least partial coating 114 of the core particle 112 is initiated before providing the Raman-active analyte 116. However, the coating 114 does not have to be completed before providing the Raman-active analyte 116. The providing of a coating 114 or coating precursor and providing of the Raman-active analyte 116 may occur simultaneously or overlap as the Raman-active analyte 116 may be provided concurrently with the completion of the coating 114, but after the coating 114 is initiated.

As previously discussed, a linker 118 such as aminopropyl trimethoxysilane (APTMS) may be added to facilitate the deposition of the coating 114 onto the core particle 112. The amino group of the aminopropyl trimethoxysilane binds to the surface of the core particle 112 while the alkoxysilane hydrolyzes, forming siloxy or hydroxy silyl groups. The hydrolyzed silane condenses with silicate in the silicate solution provided. In this way, the core particle 112 acts as a seed for growth of a silica coating. In one embodiment, a layer of silica coating 114 is deposited by adding a basic sodium silicate solution to an APTMS-modified colloidal gold core particle 112. The high surface area of the APTMS-modified colloidal gold core particle 112 provides nucleation sites onto which the silicate coating 114 may deposit. This coating reaction using basic sodium silicate is referred to as the Water-glass reaction. The coating 114 may be made thicker using the Stober process in ethanol.

In another embodiment, a method of conducting an assay is provided. The method includes attaching a Raman-active particle 110 to one or more targeted moieties. Next, the Raman spectrum of the Raman-active particle 110 is measured. The Raman spectrum is then correlated to the presence of the targeted moiety.

The targeted moiety includes, but is not limited to biological species, small molecules, particles, viruses, peptides, DNA or RNA strands, and the like.

The following examples of Raman-active particles 101 with three varying average sizes of core particle 112, three varying analytes, and two varying reactions are summarized in Table 1. The three varying average sizes of core particle 112 are 50 nm, 30 nm, and 15 nm of Au particles. The three varying analytes are MBA, BPE, and NT. The two reactions are Stober and Water Glass.

TABLE 1

| Example | Size of Au core particles (nm) | Analyte | Reaction |
| --- | --- | --- | --- |
| 1A | 50 | MBA | Stöber |
| 1B | 30 | MBA | Stöber |
| 1C | 15 | MBA | Stöber |
| 2A | 50 | MBA | Water Glass |
| 2B | 30 | MBA | Water Glass |
| 2C | 15 | MBA | Water Glass |
| 3A | 50 | BPE | Stöber |
| 3B | 30 | BPE | Stöber |
| 3C | 15 | BPE | Stöber |
| 4A | 50 | BPE | Water Glass |
| 4B | 30 | BPE | Water Glass |
| 4C | 15 | BPE | Water Glass |
| 5A | 50 | NT | Stöber |
| 5B | 30 | NT | Stöber |
| 5C | 15 | NT | Stöber |
| 6A | 50 | NT | Water Glass |
| 6B | 30 | NT | Water Glass |
| 6C | 15 | NT | Water Glass |

EXAMPLES 1A-C 50 nm, 30 nm, and 15 nm Au Particles with MBA and $SiO_2$ Coating, under Stöber Reaction A 50 mL colloidal solution comprising Au core particles was treated with 0.5 g of ion exchange resin for 30 min and filtered. The average sizes of the Au core particles were 50 nm (Example 1A), 30 nm (Example 1B), and 15 nm (Example 1C). The colloidal solution was placed in a beaker and 250 µL of 10 mM 3-aminopropyl trimethoxysilane solution was added dropwise followed by stirring for 15 minutes. Two mL of 0.54% sodium silicate solution was added slowly dropwise to the colloidal solution to form a resulting solution. 400 µL of 0.62 mM 4-Mercaptobenzoic acid solution in ethanol was provided to the resulting solution. After stirring for 15 min, the solution was allowed to sit for 24 hours. The solution was poured into 180 mL EtOH with stirring, followed by 200 µL 30% ammonium hydroxide solution and 30 µL Si(OEt)$_4$. The solution was stirred 15 min and let sit overnight. The solution was then placed into a flask and the solvent evaporated to a volume of approximately 30 mL, and then rinsed into a centrifuge tube and centrifuged for 1 hour. A pale pink supernatant liquid was decanted, leaving 3 mL total of a dark red colloid.

Figures 9, 10:
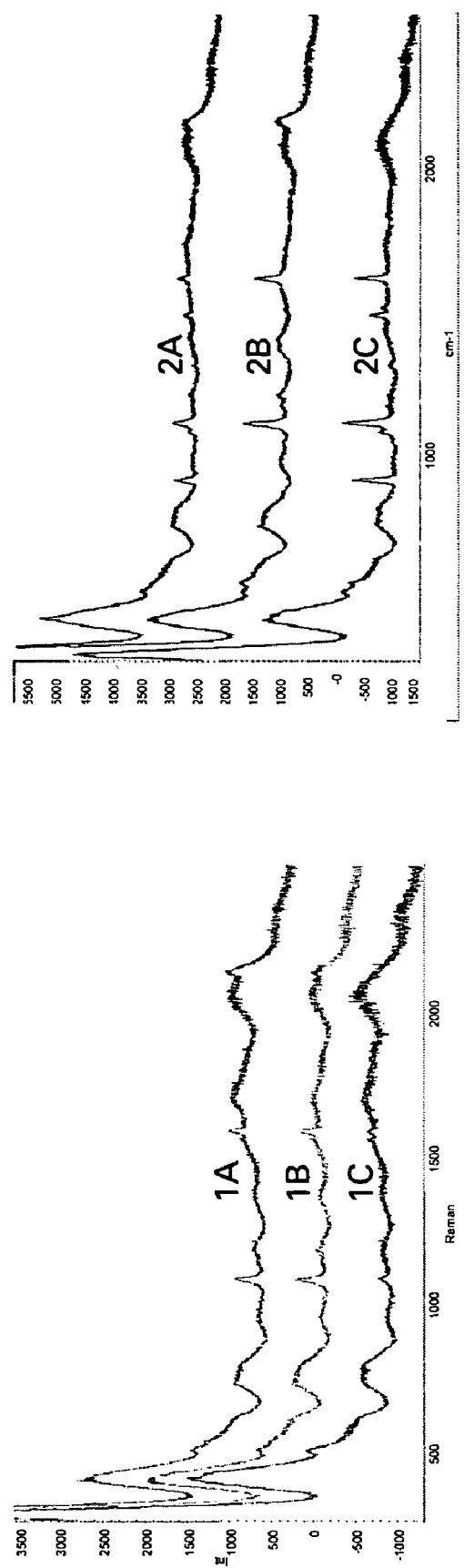
FIG. 9 are Raman spectra of an embodiment of Raman-active particles with 4-Mercaptobenzoic acid (MBA) and $SiO_2$ coating in accordance with an embodiment of the invention.
FIG. 10 are also Raman spectra of Raman-active particles with MBA and $SiO_2$ coating in accordance with an embodiment of the invention.

FIG. 9 are Raman spectra of the embodiments of the Raman-active particles 110 in Examples 1A-C with MBA analyte and SiO$_2$ coating demonstrating the activeness of the Raman-active particles 110.

Figure 15:
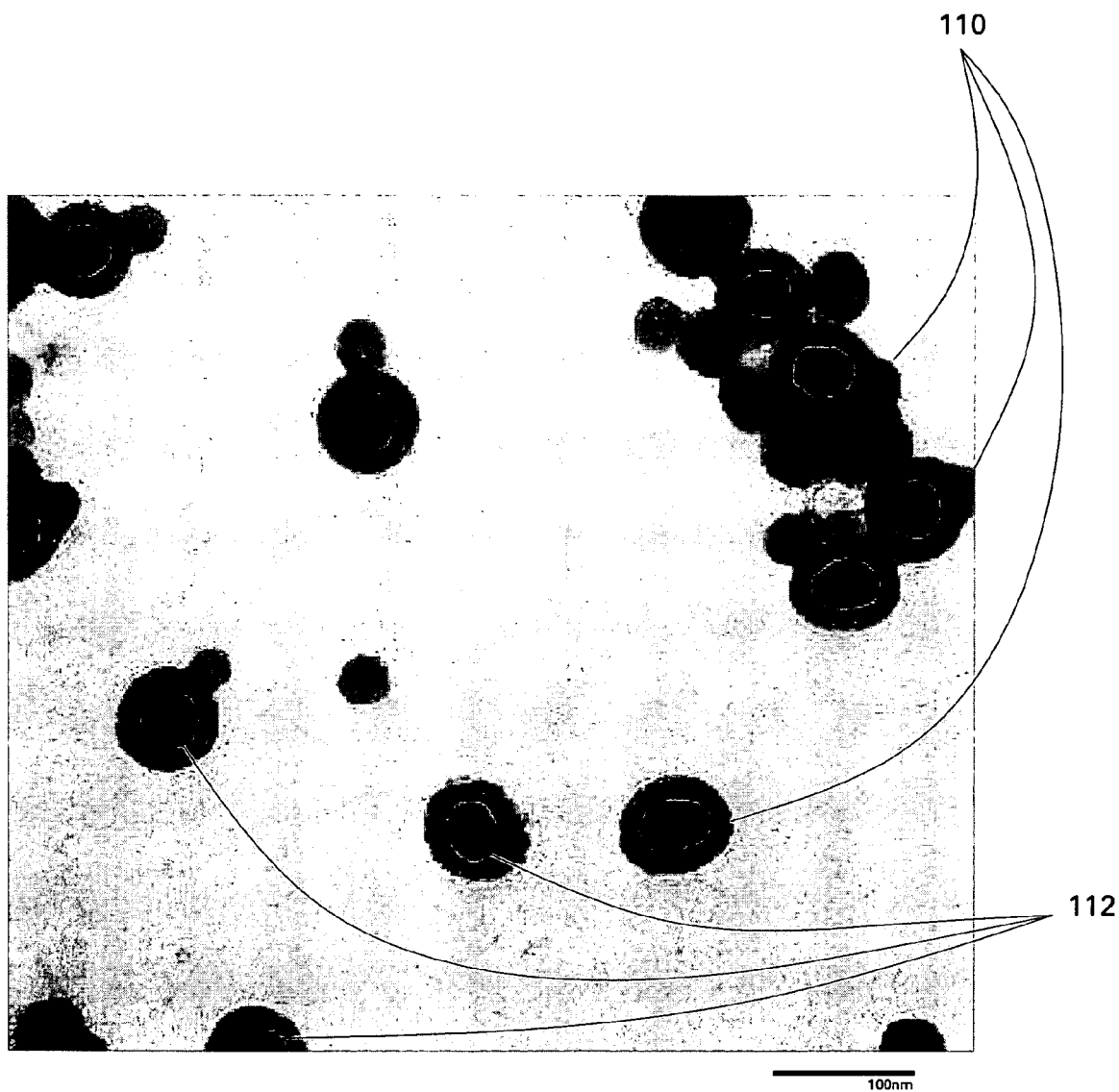
FIG. 15 are Transmission Electron Microscopic (TEM) images of Raman-active particles with MBA, $SiO_2$ coating, and core particles with an average size of 50 nm in accordance with an embodiment of the invention.
Figure 16:
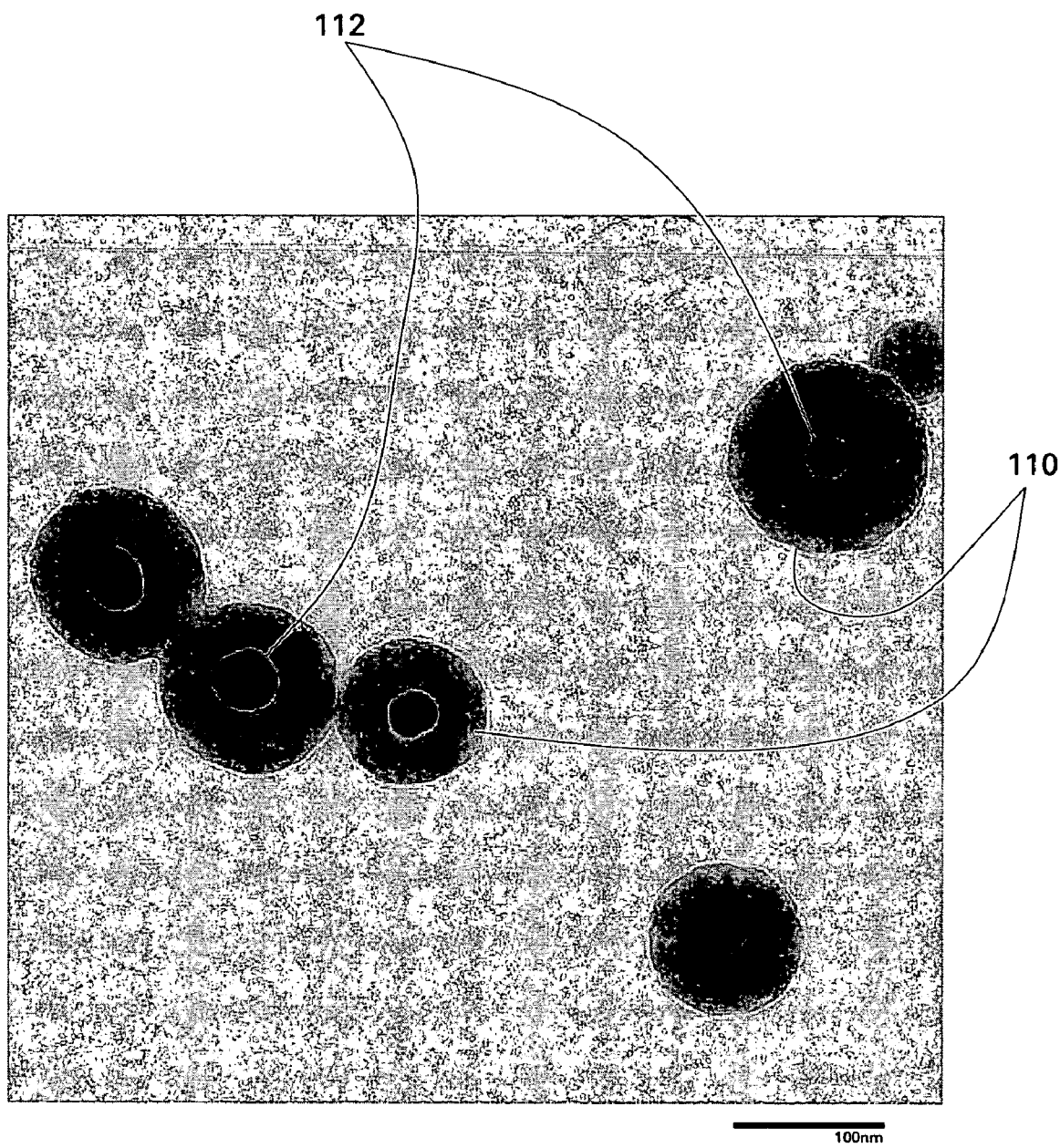
FIG. 16 are TEM images of Raman-active particles with MBA, $SiO_2$ coating, and core particles with an average size of 30 nm in accordance with an embodiment of the invention.
Figure 17:
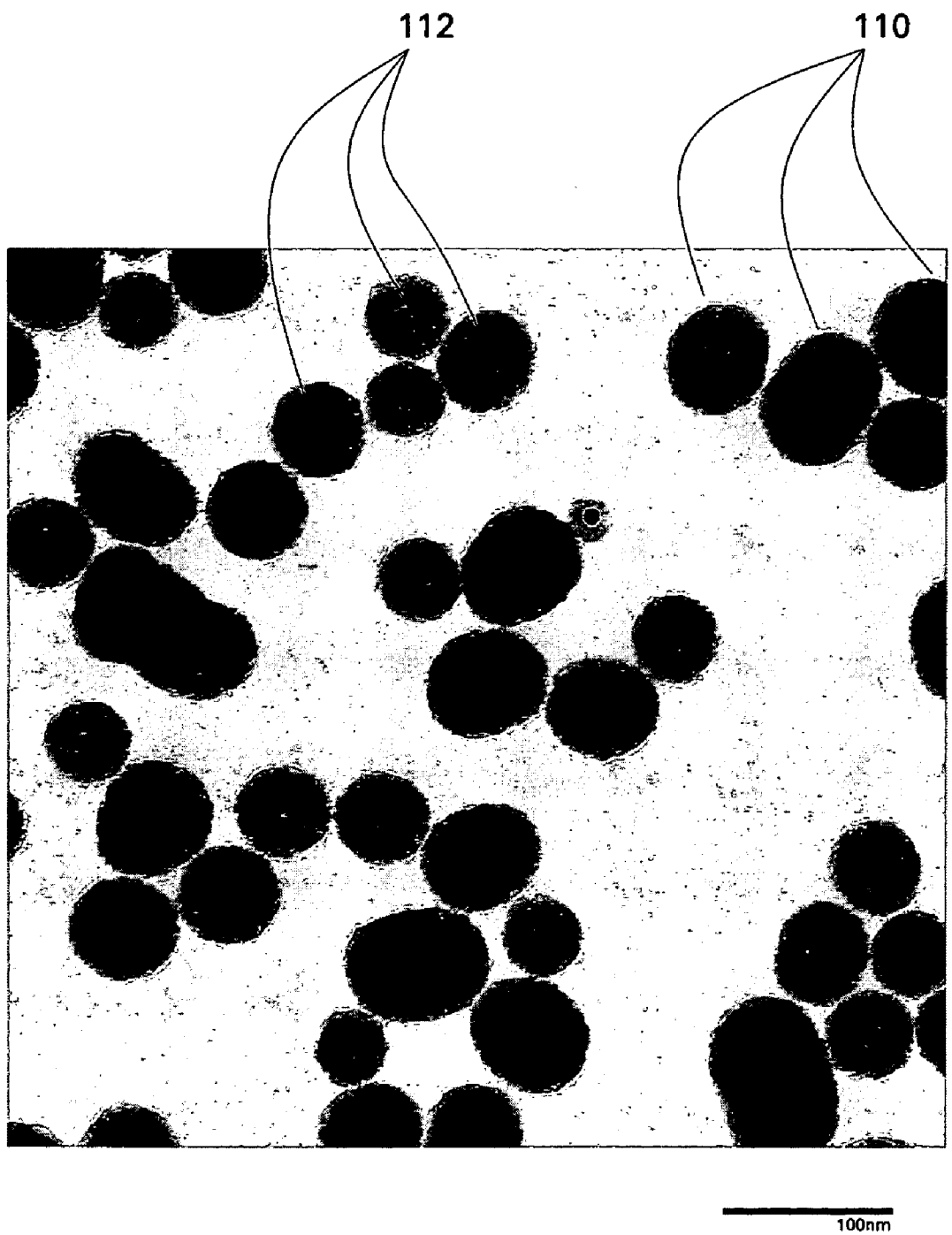
FIG. 17 are TEM images of Raman-active particles with MBA, $SiO_2$ coating, and core particles with an average size of 15 nm in accordance with an embodiment of the invention.

FIG. 15-17 are TEM images of the embodiments of Raman-active particles 110 in Examples 1A-C respectively. The TEM images demonstrate that the Raman-active particles 110 are substantially non-aggregated and nanoscale sized. The Raman-active particles 110 also have a mono-modal distribution typical of that observed in the preparation of gold colloids

EXAMPLES 2A-C 50 nm, 30 nm, and 15 nm Au particles with MBA and SiO$_2$ Coating, under Water Glass A 50 mL colloidal solution comprising Au particles was treated with 0.5 g of ion exchange resin for 30 min and filtered. The average sizes of the Au core particles were 50 nm (Example 2A), 30 nm (Example 2B), and 15 nm (Example 2C). The colloidal solution was placed in a beaker and 250 µL of 10 mM 3-aminopropyl trimethoxysilane solution was added dropwise followed by stirring for 15 minutes. Two mL of 0.54% sodium silicate solution was added slowly dropwise to the colloidal solution to form a resulting solution. 400 µL of 0.62 mM 4-Mercaptobenzoic acid solution in ethanol was provided to the resulting solution. After stirring for 15 min, the solution was allowed to sit for 7 days. The solution was rinsed into a centrifuge tube and centrifuged for 1 hour. A pale pink supernatant liquid was decanted, leaving 3 mL total of a dark red colloid.

FIG. 10 are Raman spectra of the embodiments of the Raman-active particles 110 in Examples 2A-C with MBA analyte and SiO$_2$ coating demonstrating the activeness of the Raman-active particles 110.

Figure 18:
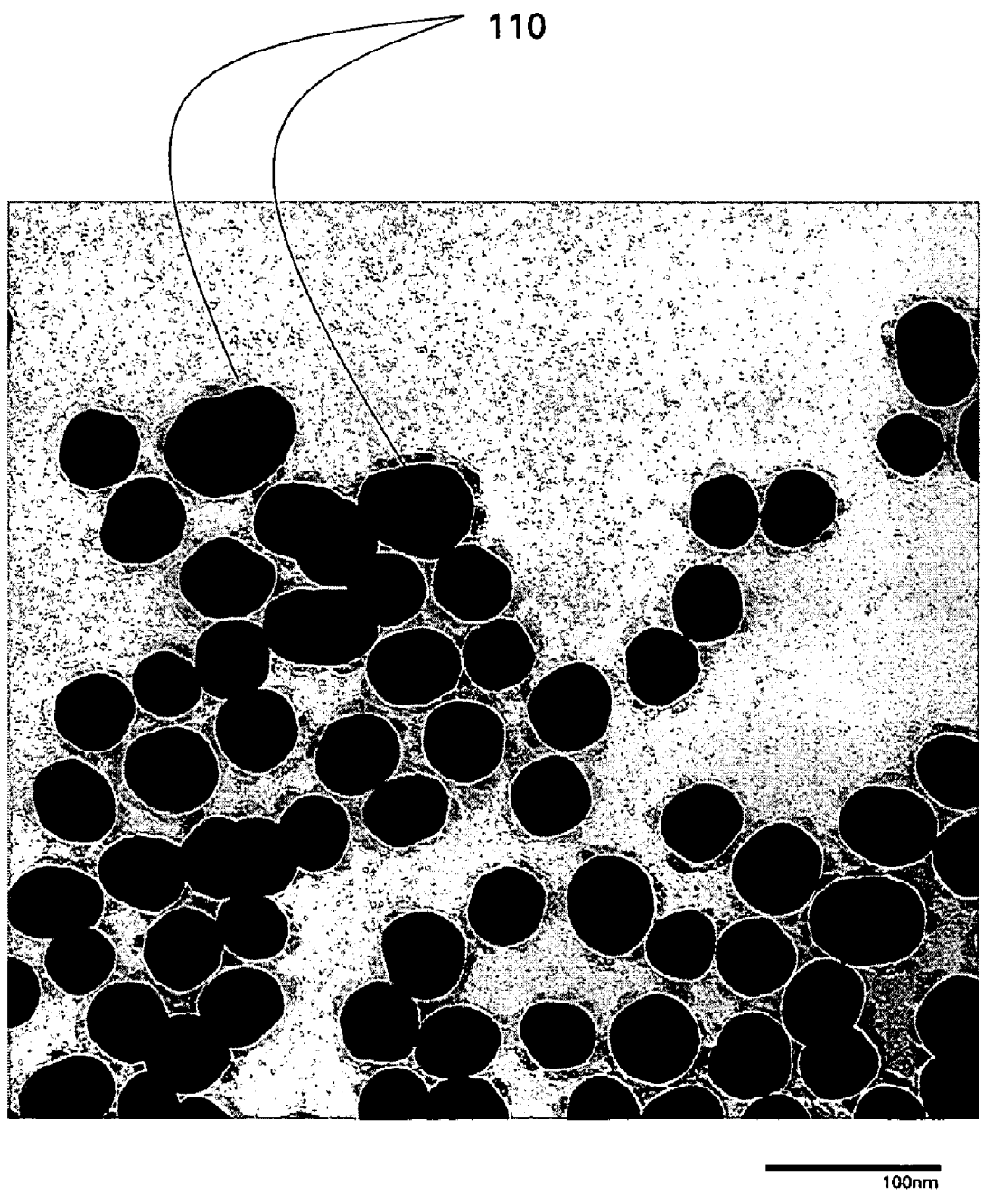
FIG. 18 are TEM images of Raman-active particles with MBA, $SiO_2$ coating, and core particles with an average size of 50 nm in accordance with an embodiment of the invention.
Figure 19:
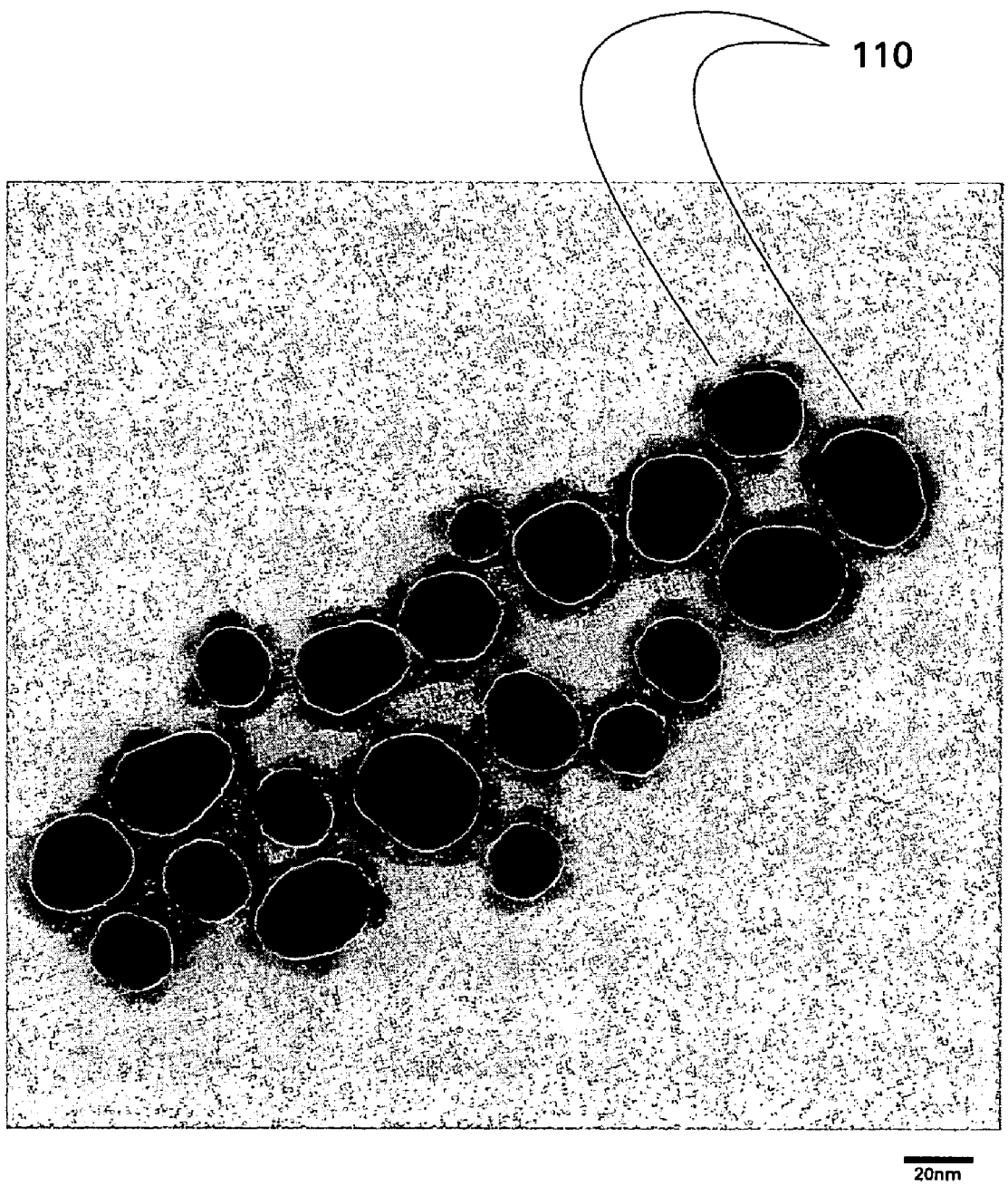
FIG. 19 are TEM images of Raman-active particles with MBA, $SiO_2$ coating, and core particles with an average size of 30 nm in accordance with an embodiment of the invention.
Figure 20:
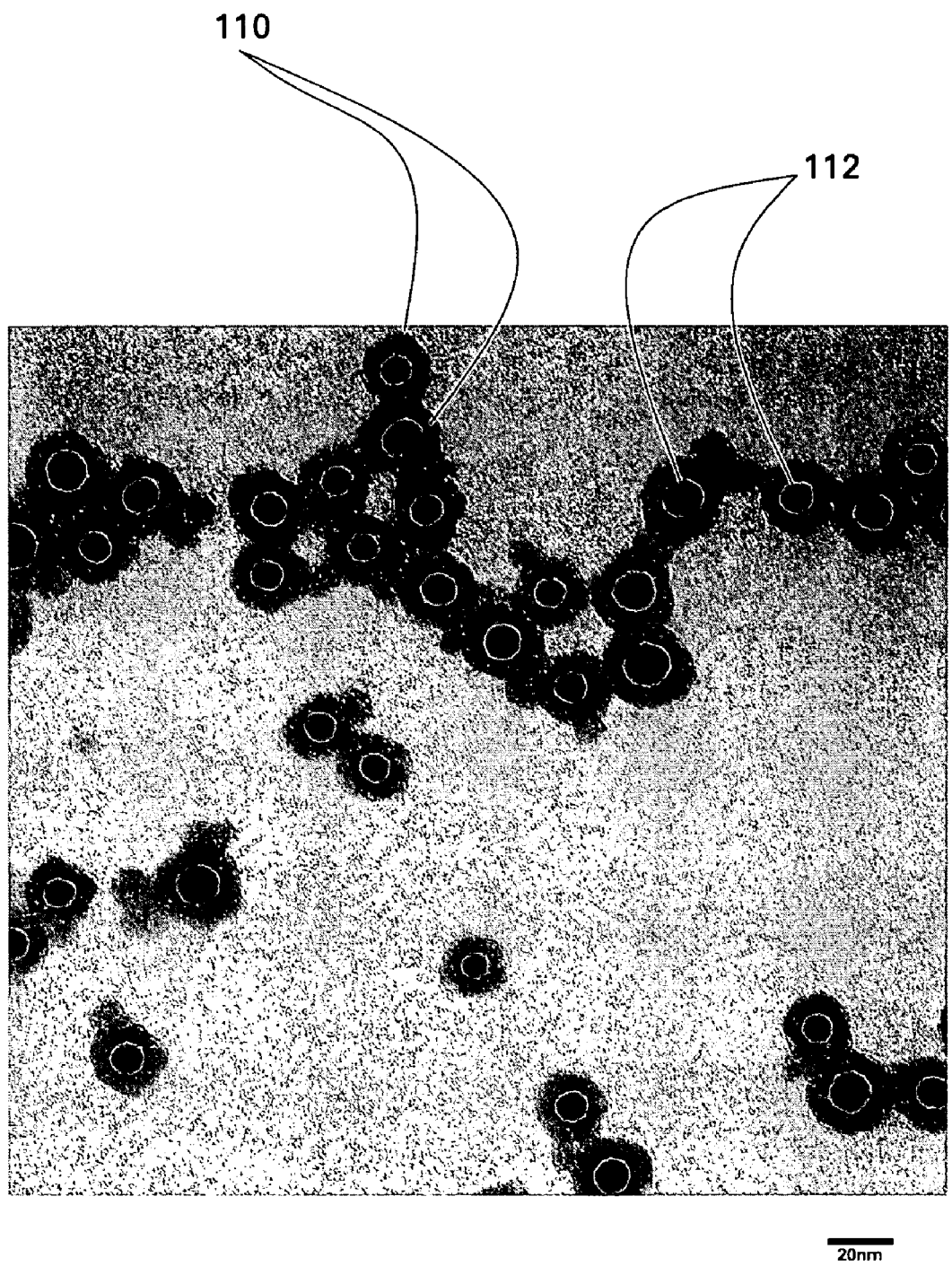
FIG. 20 are TEM images of Raman-active particles with MBA, $SiO_2$ coating, and core particles with an average size of 10 nm in accordance with an embodiment of the invention.

FIG. 18-20 are TEM images of the embodiments of Raman-active particles 110 in Example 2A-C respectively. The TEM images demonstrate that the Raman-active particles 110 are substantially non-aggregated and nanoscale sized. The Raman-active particles 110 also have a mono-modal distribution typical of that observed in the preparation of gold colloids

EXAMPLES 3A-C 50 nm, 30 nm, and 15 nm Au Particles with BPE and SiO$_2$ Coating, under Stöber A 50 mL colloidal solution comprising Au particles was treated with 0.5 g of ion exchange resin for 30 min and filtered. The average sizes of the Au core particles were 50 nm (Example 3A), 30 nm (Example 3B), and 15 nm (Example 3C). The colloidal solution was placed in a beaker and 250 µL of 10 mM 3-aminopropyl trimethoxysilane solution was added dropwise followed by stirring for 15 minutes. Two mL of 0.54% sodium silicate solution was added slowly dropwise to the colloidal solution to form a resulting solution. 250 µL of 1.0 mM trans-bis(pyridyl) ethylene solution in ethanol was provided to the resulting solution. After stirring for 15 min, the resulting solution was allowed to sit for 24 hours. The solution was poured into 180 mL EtOH with stirring, followed by 200 µL 30% ammonium hydroxide solution and 30 µL Si(OEt)$_4$. The solution was stirred 15 min and let sit overnight. The solution was then placed into a flask and the solvent evaporated to a volume of approximately 30 mL, and then rinsed into a centrifuge tube and centrifuged for 1 hour. A pale pink supernatant liquid was decanted, leaving 3 mL total of a dark red colloid.

Figure 11:
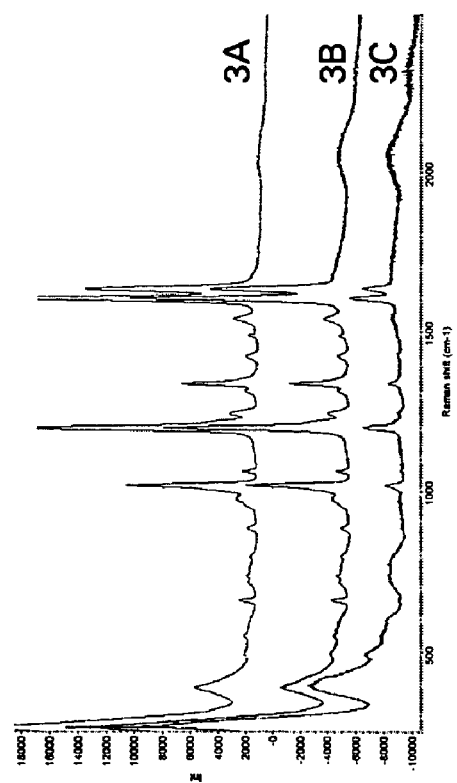
FIG. 11 are Raman spectra of Raman-active particles with trans-bis(pyridyl)ethylene (BPE) and $SiO_2$ coating in accordance with an embodiment of the invention.

FIG. 11 are Raman spectra of the embodiments of the Raman-active particles 110 in Examples 3A-C with BPE analyte and SiO$_2$ coating demonstrating the activeness of the Raman-active particles 110.

EXAMPLES 4A-C 50 nm, 30 nm, and 15 nm Au Particles with BPE and SiO$_2$ Coating, Under Water Glass A 50 mL colloidal solution comprising Au particles was treated with 0.5 g of ion exchange resin for 30 min and filtered. The average sizes of the Au core particles were 50 nm (Example 4A), 30 nm (Example 4B), and 15 nm (Example 4C). The colloidal solution was placed in a beaker and 250 µL of 10 mM 3-aminopropyl trimethoxysilane solution was added dropwise followed by stirring for 15 minutes. Two mL of 0.54% sodium silicate solution was added slowly dropwise to the colloidal solution to form a resulting solution. 250 µL of 1.0 mM trans-bis(pyridyl) ethylene solution in ethanol was provided to the resulting solution. After stirring for 15 min, the solution was allowed to sit for 7 days. The solution was rinsed into a centrifuge tube and centrifuged for 1 hour. A pale pink supernatant liquid was decanted, leaving 3 mL total of a dark red colloid.

Figure 12:
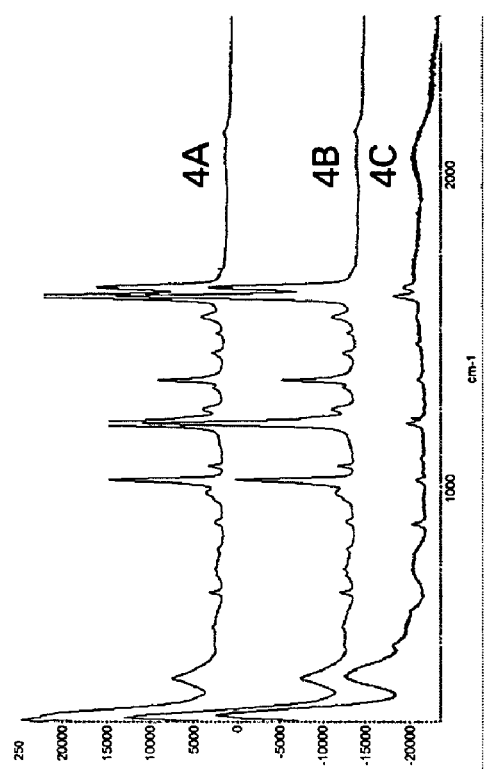
FIG. 12 are also Raman spectra of Raman-active particles with BPE and $SiO_2$ coating in accordance with an embodiment of the invention.

FIG. 12 are Raman spectra of the embodiments of the Raman-active particles 110 in Examples 4A-C with BPE analyte and SiO$_2$ coating demonstrating the activeness of the Raman-active particles 110.

EXAMPLES 5A-C 50 nm, 30 nm, and 15 nm Au particles with NT and SiO$_2$ Coating, Under Stöber A 50 mL colloidal solution comprising Au particles was treated with 0.5 g of ion exchange resin for 30 min and filtered. The average sizes of the Au core particles were 50 nm (Example 5A), 30 nm (Example 5B), and 15 nm (Example 5C). The colloidal solution was placed in a beaker and 250 µL of 10 mM 3-aminopropyl trimethoxysilane solution was added dropwise followed by stirring for 15 minutes. Two mL of 0.54% sodium silicate solution was added slowly dropwise to the colloidal solution to form a resulting solution. 500 µL of 0.5 mM naphthalene thiol solution in ethanol was provided to the resulting solution. After stirring for 15 min, the resulting solution was allowed to sit for 24 hours. The solution was poured into 180 mL EtOH with stirring, followed by 200 µL 30% ammonium hydroxide solution and 30 µL Si(OEt)$_4$. The solution was stirred 15 min and let sit overnight. The solution was then placed into a flask and the solvent evaporated to a volume of approximately 30 mL, and then rinsed into a centrifuge tube and centrifuged for 1 hour. A pale pink supernatant liquid was decanted, leaving 3 mL total of a dark red colloid.

Figure 13:
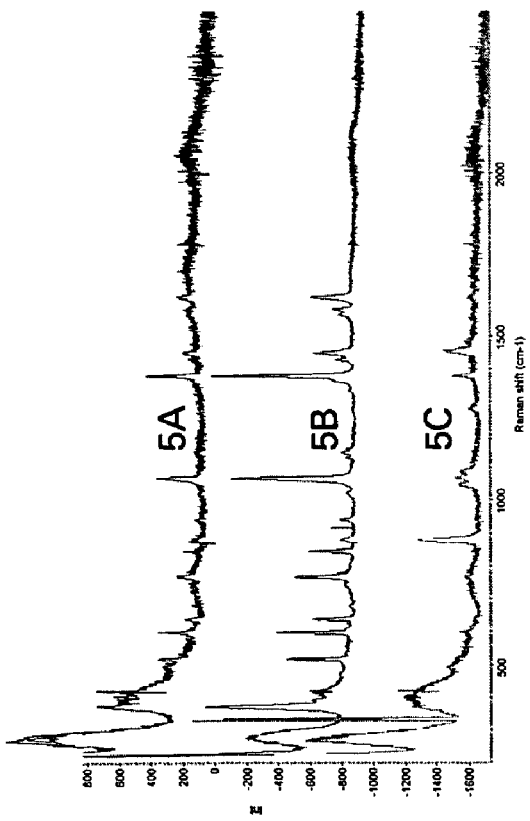
FIG. 13 are Raman spectra of Raman-active particles with naphthalene thiol (NT) and $SiO_2$ coating in accordance with an embodiment of the invention.

FIG. 13 are Raman spectra of the embodiments of the Raman-active particles 110 in Examples 5A-C with NT analyte and $SiO_2$ coating demonstrating the activeness of the Raman-active particles 110.

EXAMPLE 6A-C 50 nm, 30 nm, and 15 nm Au Particles with NT and $SiO_2$ Coating, Under Water Glass A 50 mL colloidal solution comprising Au particles was treated with 0.5 g of ion exchange resin for 30 min and filtered. The average sizes of the Au core particles were 50 nm (Example 6A), 30 nm (Example 6B), and 15 nm (Example 6C). The colloidal solution was placed in a beaker and 250 μL of 10 mM 3-aminopropyl trimethoxysilane solution was added dropwise followed by stirring for 15 minutes. Two mL of 0.54% sodium silicate solution was added slowly dropwise to the colloidal solution to form a resulting solution. 500 μL of 0.5 mM naphthalene thiol solution in ethanol was provided to the resulting solution. After stirring for 15 min, the solution was allowed to sit for 7 days. The solution was rinsed into a centrifuge tube and centrifuged for 1 hour. A pale pink supernatant liquid was decanted, leaving 3 mL total of a dark red colloid.

Figure 14:
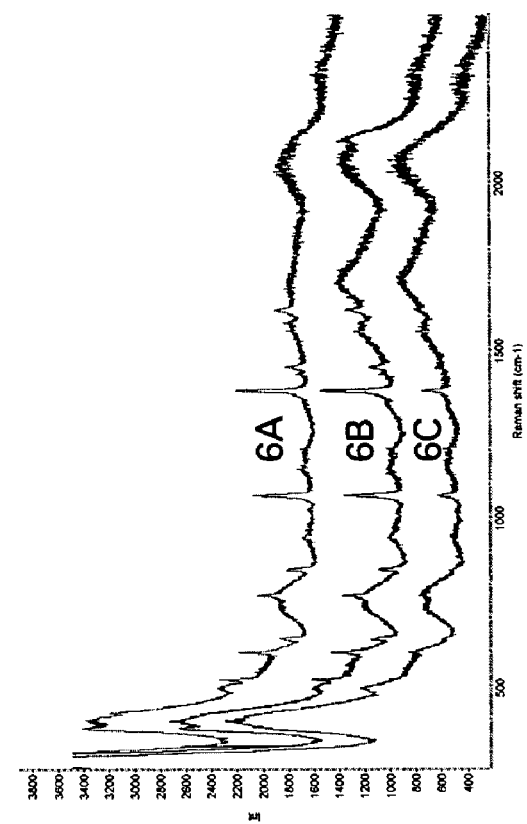
FIG. 14 are also Raman spectra of Raman-active particles with NT and $SiO_2$ coating in accordance with an embodiment of the invention.

FIG. 14 are Raman spectra of the embodiments of the Raman-active particles 110 in Examples 6A-C with NT analyte and $SiO_2$ coating demonstrating the activeness of the Raman-active particles 110.

While the invention has been described in detail in connection with only a limited number of aspects, it should be readily understood that the invention is not limited to such disclosed aspects. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A Raman-active particle comprising:
   a core particle;
   a coating substantially covering the core particle; and
   a plurality of Raman-active analytes at least partially within the coating and comprising analytes of different types.

2. The Raman-active particle of claim 1, wherein the core particle comprises at least one metal selected from a group consisting of Au, Ag, Cu, Ni, Pd, Pt, Na, Al, and Cr.

3. The Raman-active particle of claim 2, wherein the core particle comprises an Au core particle.

4. The Raman-active particle of claim 2, wherein the core particle comprises a metallic surface.

5. The Raman-active particle of claim 1, wherein the Raman-active particle has a diameter up to about 1000 nm.

6. The Raman-active particle of claim 1, wherein the core particle has a diameter up to about 500 nm.

7. The Raman-active particle of claim 1, wherein the coating has a thickness in a range from about 1 nm to about 500 nm.

8. The Raman-active particle of claim 1, wherein the plurality of Raman-active analytes comprise at least one Raman-active analyte selected from a group consisting of 4-mercaptopyridine, 2-mercaptopyridine, trans-bis(pyridyl) ethylene, naphthalene thiol, and mercaptobenzoic acid.

9. The Raman-active particle of claim 1, wherein the plurality of Raman-active analytes are embedded within the coating.

10. The Raman-active particle of claim 1, wherein the plurality of Raman-active analytes are dispersed within the coating.

11. The Raman-active particle of claim 1, wherein the coating comprises a multilayer coating.

12. The Raman-active particle of claim 1, wherein the coating is substantially inorganic.

13. The Raman-active particle of claim 1, wherein the coating comprises an elemental oxide, wherein at least one element of the elemental oxide comprises silicon.

14. The Raman-active particle of claim 13, wherein the coating comprises substantially silica.

15. The Raman-active particle of claim 1, further comprising a linker.

16. The Raman-active particle of claim 15, wherein the linker comprises an alkoxysilane.

17. A Raman-active particle comprising:
   a) a core particle comprising a metallic surface;
   b) a coating substantially covering the core particle, wherein the coating comprises an elemental oxide, wherein at least one element of the elemental oxide comprises silicon; and
   c) a plurality of Raman-active analytes at least partially within the coating and comprising analytes of different types.

18. The Raman-active particle of claim 17, wherein the Raman-active particle has a diameter up to about 1000 nm.

19. The Raman-active particle of claim 17, wherein the core particle has a diameter up to about 500 nm.

20. The Raman-active particle of claim 17, wherein the plurality of Raman-active analytes are embedded within the coating.

21. The Raman-active particle of claim 17, wherein the plurality of Raman-active analytes are dispersed within the coating.

22. The Raman-active particle of claim 17, wherein the coating comprises a multilayer coating.

23. The Raman-active particle of claim 17, further comprising a linker, wherein the linker comprises an alkoxysilane.

* * * * *